US008939581B2

United States Patent
Takai et al.

(10) Patent No.: US 8,939,581 B2
(45) Date of Patent: Jan. 27, 2015

(54) OPHTHALMOLOGIC PHOTOGRAPHING APPARATUS

(75) Inventors: Motoya Takai, Nagareyama (JP); Kyoji Sekiguchi, Utsunomiya (JP); Hajime Nakajima, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 306 days.

(21) Appl. No.: 13/419,227

(22) Filed: Mar. 13, 2012

(65) Prior Publication Data

US 2012/0169996 A1    Jul. 5, 2012

Related U.S. Application Data

(63) Continuation of application No. 12/869,348, filed on Aug. 26, 2010, now Pat. No. 8,157,377.

(30) Foreign Application Priority Data

Aug. 31, 2009 (JP) ................................ 2009-199969

(51) Int. Cl.
*A61B 3/14* (2006.01)
*A61B 3/10* (2006.01)
*A61B 3/12* (2006.01)
*A61B 3/18* (2006.01)

(52) U.S. Cl.
CPC ... *A61B 3/12* (2013.01); *A61B 3/14* (2013.01); *A61B 3/185* (2013.01)
USPC ............................ 351/206; 351/216; 351/246

(58) Field of Classification Search
CPC .......................................................... A61B 3/14
USPC .................................. 351/206, 216–217, 244
See application file for complete search history.

(56) References Cited

U.S. PATENT DOCUMENTS

| 5,337,095 A * | 8/1994 | Katsuragi et al. ............. 351/208 |
| 8,157,377 B2 * | 4/2012 | Takai et al. ................... 351/208 |
| 2009/0244483 A1 * | 10/2009 | Yoshino et al. ............... 351/206 |
| 2011/0267583 A1 * | 11/2011 | Hayashi ........................ 351/206 |

FOREIGN PATENT DOCUMENTS

| JP | 2011050439 A | | 3/2011 |
| WO | WO 2010/079550 | * | 7/2010 |

* cited by examiner

*Primary Examiner* — Jordan Schwartz
(74) *Attorney, Agent, or Firm* — Canon USA, Inc. IP Division

(57) ABSTRACT

An ophthalmologic photographing apparatus includes an optical system, a pedestal, an auxiliary lens configured to be able to be inserted into and retracted from the optical system, a focusing lens, a focusing lens driving unit configured to move the focusing lens along an optical axis, a pedestal position detection unit configured to detect that the pedestal is away from the subject's eye by a predetermined distance, an auxiliary lens insertion detection unit configured to detect that the auxiliary lens is inserted into the optical system, a storage unit configured to store a position of the focusing lens, and a control unit configured to cause the focusing lens driving unit to move the focusing lens to a predetermined position stored in the storage unit based on outputs from the pedestal position detection unit and the auxiliary lens insertion detection unit.

8 Claims, 5 Drawing Sheets

OPHTHALMOLOGIC PHOTOGRAPHING APPARATUS

CROSS REFERENCE TO RELATED APPLICATIONS

This application is a Continuation of U.S. patent application Ser. No. 12/869,348 filed Aug. 26, 2010, which claims priority to Japanese Patent Application No. 2009-199969 filed Aug. 31, 2009, both of which are hereby incorporated by reference herein in their entireties.

BACKGROUND OF THE INVENTION

1. Field of the Invention

The present invention relates to an ophthalmologic photographing apparatus that is used in an ophthalmic office for observing and photographing a fundus and an anterior segment of a subject's eye.

2. Description of the Related Art

There has conventionally been known an ophthalmologic photographing apparatus, as discussed in Japanese Patent Application Laid-Open No. 6-254054, in which observation of a fundus can be changed to observation of an anterior segment by inserting an auxiliary lens optical system into an optical path of an observation/photographing optical system according to the position of a pedestal that can be moved backward and forward and right and left relative to a subject's eye.

In this case, during the observation of the fundus, the pedestal is made close to the subject's eye, and the auxiliary lens optical system is retracted to the outside of the optical path to observe and photograph the fundus. On the other hand, during the observation of the anterior segment, the pedestal is moved away from the subject's eye and the auxiliary lens optical system is inserted into the optical path to observe and photograph the anterior segment.

However, in the above ophthalmologic photographing apparatus, a focusing lens is required to be readjusted with the inserting and retracting movement of the auxiliary lens optical system, when the changeover between the observation/photographing of the fundus and the observation/photographing of the anterior segment is performed, which means the operation is troublesome.

SUMMARY OF THE INVENTION

The present invention is directed to an ophthalmologic photographing apparatus that does not need to readjust a focusing lens during a changeover of observation and photographing, and that facilitates the changeover of observation and photographing.

According to an aspect of the present invention, an ophthalmologic photographing apparatus includes an optical system configured to be used to observe and photograph a subject's eye, a pedestal configured to move the optical system backward and forward and right and left relative to the subject's eye, an auxiliary lens configured to be able to be inserted into and retracted from the optical system, a focusing lens configured to focus the optical system on the subject's eye, a focusing lens driving unit configured to move the focusing lens along an optical axis, a pedestal position detection unit configured to detect that the pedestal is away from the subject's eye by a predetermined distance, an auxiliary lens insertion detection unit configured to detect that the auxiliary lens is inserted into the optical system, a storage unit configured to store a position of the focusing lens, and a control unit configured to cause the focusing lens driving unit to move the focusing lens to a predetermined position stored in the storage unit based on outputs from the pedestal position detection unit and the auxiliary lens insertion detection unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
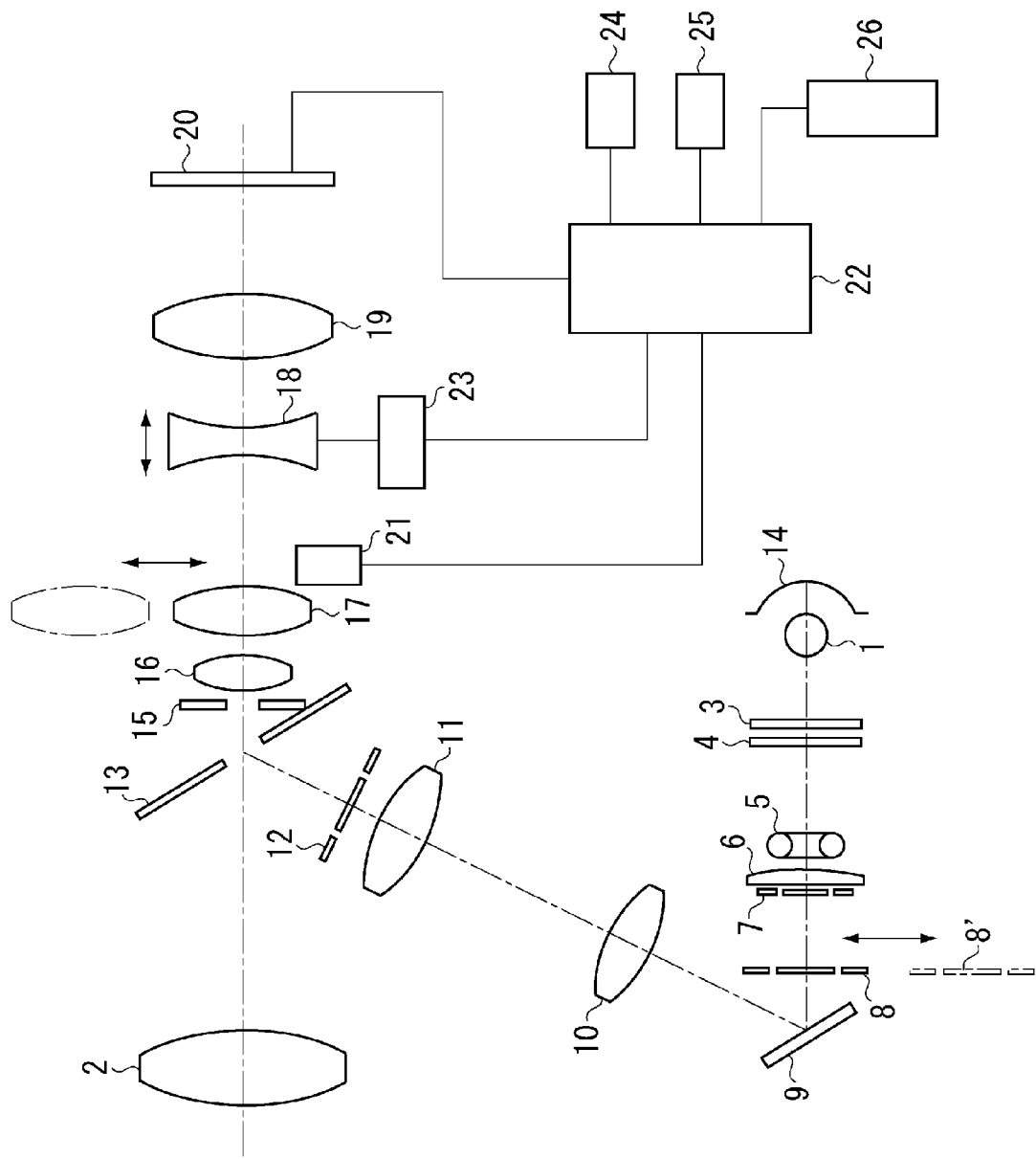
FIG. 1 is a diagram illustrating a configuration of an ophthalmologic photographing apparatus according to an exemplary embodiment of the present invention.

FIG. 1 illustrates a configuration of an ophthalmologic photographing apparatus configured to observe and photograph a subject's eye. The ophthalmologic photographing apparatus includes an illumination optical system including components from a halogen lamp 1, which serves as an illumination light source for observation, to an objective lens 2. Specifically, arranged to the halogen lamp 1 are a visible-light cut filter 3, a diffusion plate 4, a xenon tube 5, a lens 6, a pupil diaphragm having an annular opening, a crystalline lens diaphragm 8 configured to be able to be inserted to or retracted from an optical path and having an annular opening, and a mirror 9. Relay lenses 10 and 11, a cornea diaphragm 12 having an annular opening, and a perforated mirror 13 are sequentially arranged in the reflecting direction of the mirror 9. A reflection mirror 14 is provided at the rear of the halogen lamp 1.

In an optical system for observation and photographing at the rear of the perforated mirror 13, there are arranged a photographic diaphragm 15, a diopter correction lens 16 that can be inserted into or retracted from an optical path, and that enlarges a focusing range, an auxiliary lens 17 for enlarging magnification configured to be able to be inserted into or retracted from the optical path, a focusing lens 18 configured to move along the optical axis, an imaging lens 19, and an imaging unit 20. An auxiliary lens insertion detection unit 21 that detects whether the auxiliary lens 17 is inserted into the optical path is provided in the vicinity of the auxiliary lens 17.

The output of the imaging unit 20 is connected to a control unit 22. The control unit 22 is connected to the auxiliary lens insertion detection unit 21, a focusing lens driving unit 23, a monitor 24, a pedestal position detection unit 25 including a microswitch for detecting the position of the pedestal, and a photographing switch 26.

During the observation, a light flux emitted from the halogen lamp 1 is made into infrared light in which light in a visible-light wavelength area is cut by the visible light cut filter 3, and the resultant passes through the diffusion plate 4, the xenon tube 5, the lens 6, the pupil diaphragm 7, and the crystalline lens diaphragm 8 to be incident on the mirror 9. The light flux reflected by the mirror 9 passes through the relay lenses 10 and 11, and the cornea diaphragm 12, reflected on the perforated mirror 13, and then, incident on a not-illustrated subject's eye through the objective lens 2. During the photographing, the visible colored light emitted from the xenon tube 5 is incident on the subject's eye through the optical path similar to that of the infrared light.

The light flux reflected on the subject's eye passes through the objective lens 2, and then, passes through the holes of the perforated mirror 13 to be imaged on the imaging unit 20 through the photographic diaphragm 15, the diopter correction lens 16, the auxiliary lens 17, the focusing lens 18, and the imaging lens 19.

Figure 2A:
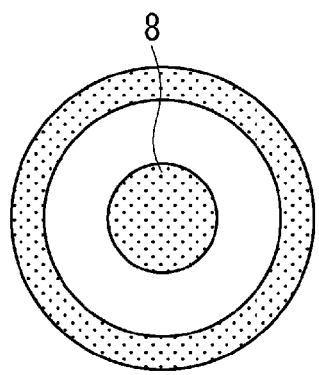
FIGS. 2A and 2B are front views of a crystalline lens diaphragm.
Figure 2B:
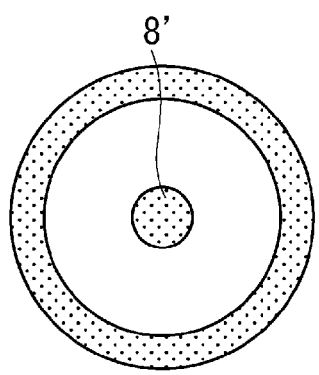

When the mydriasis of the subject's eye is insufficient, the crystalline lens diaphragm 8 illustrated in FIG. 2A can be replaced by a crystalline lens diaphragm 8' illustrated in FIG. 2B in which a central light-shielding portion is decreased to enlarge the area of the opening portion.

Figure 3:
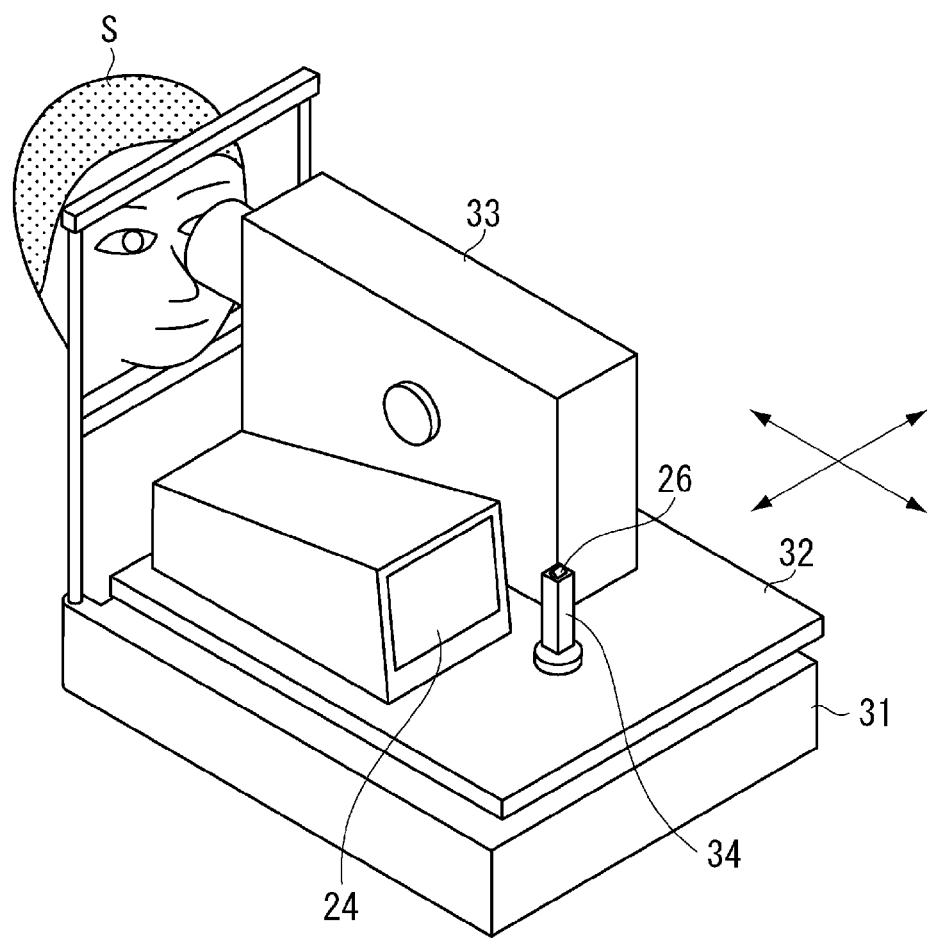
FIG. 3 is an outer appearance of the ophthalmologic photographing apparatus.

FIG. 3 is a diagram illustrating an outer appearance of the ophthalmologic photographing apparatus according to the present exemplary embodiment. A pedestal 32 that can be moved backward and forward and right and left as indicated by arrows is placed on a base 31. A main body 33 having incorporated therein the optical system of the ophthalmologic photographing apparatus illustrated in FIG. 1 and the monitor 24 are placed on the pedestal 32. The pedestal 32 is provided with an operation stick 34 having the photographing switch 26 formed on its top. The pedestal position detection unit 25 is mounted between the base 31 and the pedestal 32.

Figure 4:
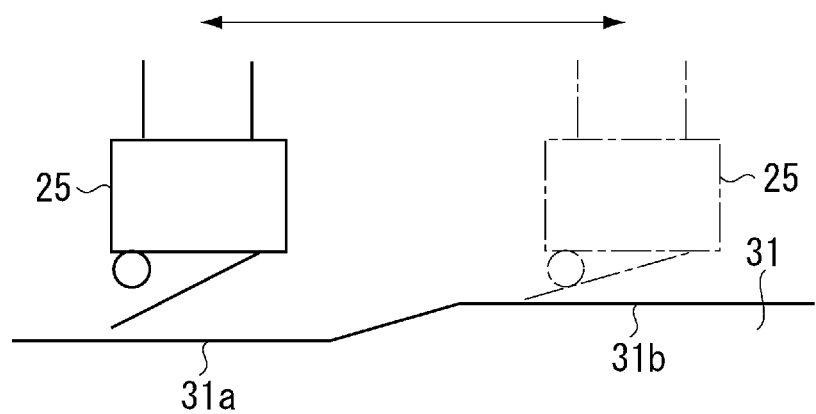
FIG. 4 is a diagram illustrating a configuration of a pedestal position detection unit.

FIG. 4 is a diagram illustrating a configuration of the pedestal position detection unit 25. A height difference is formed in the longitudinal direction on the top surface of the base 31, wherein a low portion 31a and a high portion 31b are formed. The pedestal position detection unit 25 mounted on the bottom surface of the pedestal 32 is turned off when it is located above the low portion 31a of the base 31, while it is turned on when it is located above the high portion 31b. Specifically, since the low portion 31a on the bottom surface of the base 31 is provided at the side of the subject S, while the high portion 31b is provided at the operator side, the position of the pedestal 32 can be detected by detecting on/off of the pedestal position detection unit 25.

Figure 5:
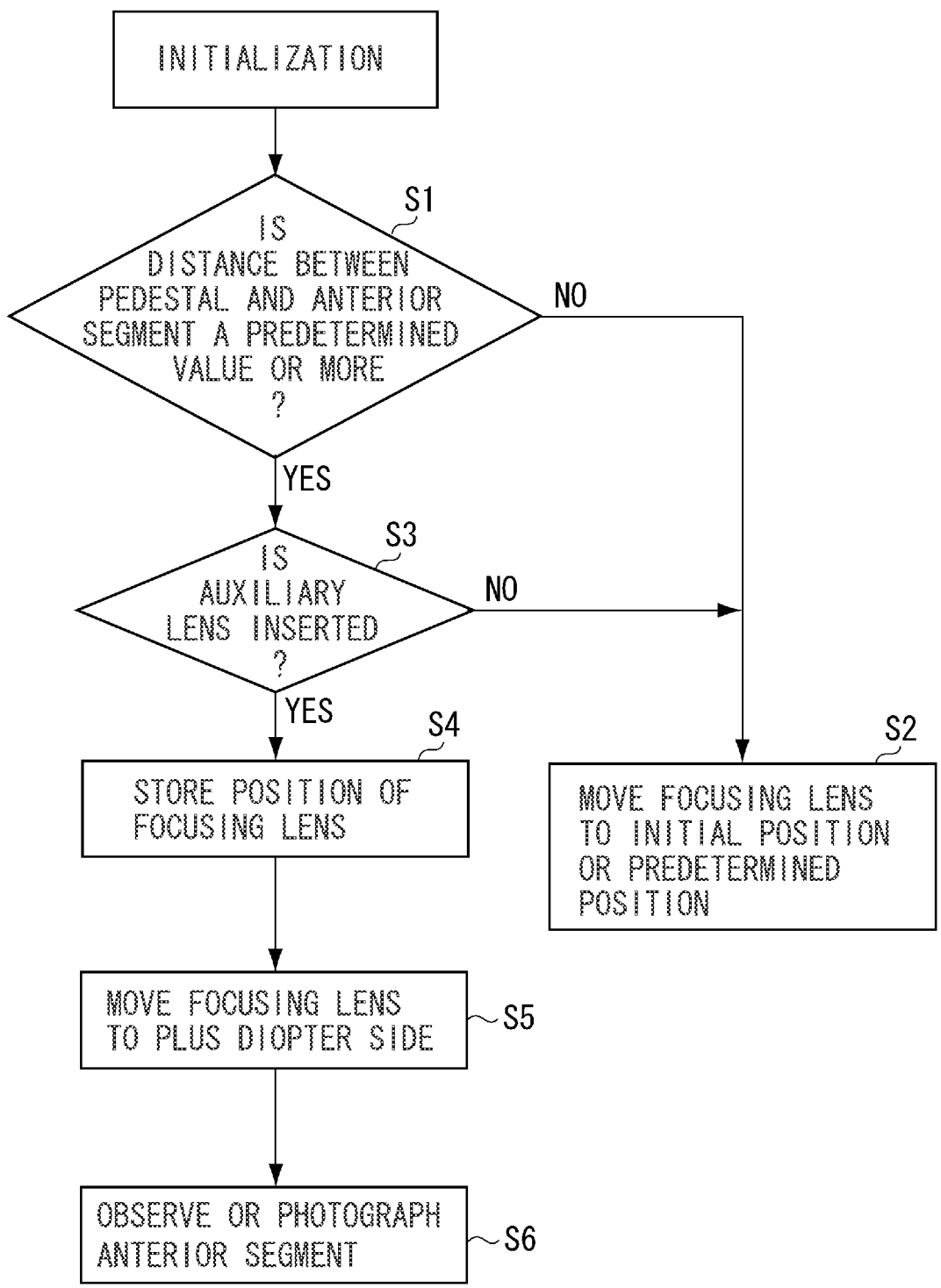
FIG. 5 is a flowchart illustrating an operation of observing and photographing an anterior segment.

FIG. 5 is a flowchart illustrating the operation of observing an anterior segment and photographing the anterior segment. When the operator observes and photographs the anterior segment of the subject S, the operator firstly operates to allow the main body 33 to be away from the subject S with the use of the operation stick 34 and the pedestal position detection unit 25. In this operation, the respective parts are initialized by the control unit 22, and then, the distance between the subject S and the pedestal 32 is confirmed by the pedestal position detection unit 25 in step S1, whereby the control unit 22 detects that the main body 33 is away from the subject S by a predetermined value or more. When it is determined that the distance between the subject S and the pedestal 32 is less than the predetermined value (NO in step S1), the control unit 22 returns the focusing lens 18 to the initial position or moves the focusing lens 18 to a predetermined position in step S2.

When it is determined that the distance between the subject S and the pedestal 32 is the predetermined value or more (YES in step S1), the control unit 22 determines in step S3 whether the auxiliary lens 17 that changes the photographing magnification is inserted into the optical path. When the auxiliary lens 17 is detected by the auxiliary lens insertion detection unit 21, which means that the auxiliary lens 17 is inserted (YES in step S3), the processing proceeds to step S4. When it cannot be detected in step S3 that the auxiliary lens 17 is inserted into the optical path (NO in step S3), the processing proceeds to step S2.

When the main body 33 is moved away from the subject S, and the auxiliary lens 17 is inserted into the optical path, the control unit 22 detects the position of the focusing lens 18 at this time and stores the position into a focus position storing unit in the control unit 22.

Next, in step S5, the control unit 22 moves the focusing lens 18 toward the plus diopter at the side of the auxiliary lens 17 along the optical path by the focusing lens driving unit 23, whereby the focusing lens 18 is moved in the range where the anterior segment of the subject's eye can be focused. In step S6, the operator observes and photographs the anterior segment.

The operator performs the above-mentioned operation to observe the anterior segment on the monitor 24. When the anterior segment is photographed after the observation, the operator confirms that the photographing range and focusing are satisfactory, and then, operates the photographing switch 26 to photograph a still image of the anterior segment. The reflectivity of the photographic light is different in general between the anterior segment and the fundus. Therefore, the anterior segment is irradiated with a light quantity corresponding to the anterior segment.

In the present exemplary embodiment, the optical system is unambiguously fixed during the photographing of the anterior segment as described above, whereby the photographing magnification is kept constant, which is suitable for comparing the image to a previous image or measuring the image.

Figure 6:
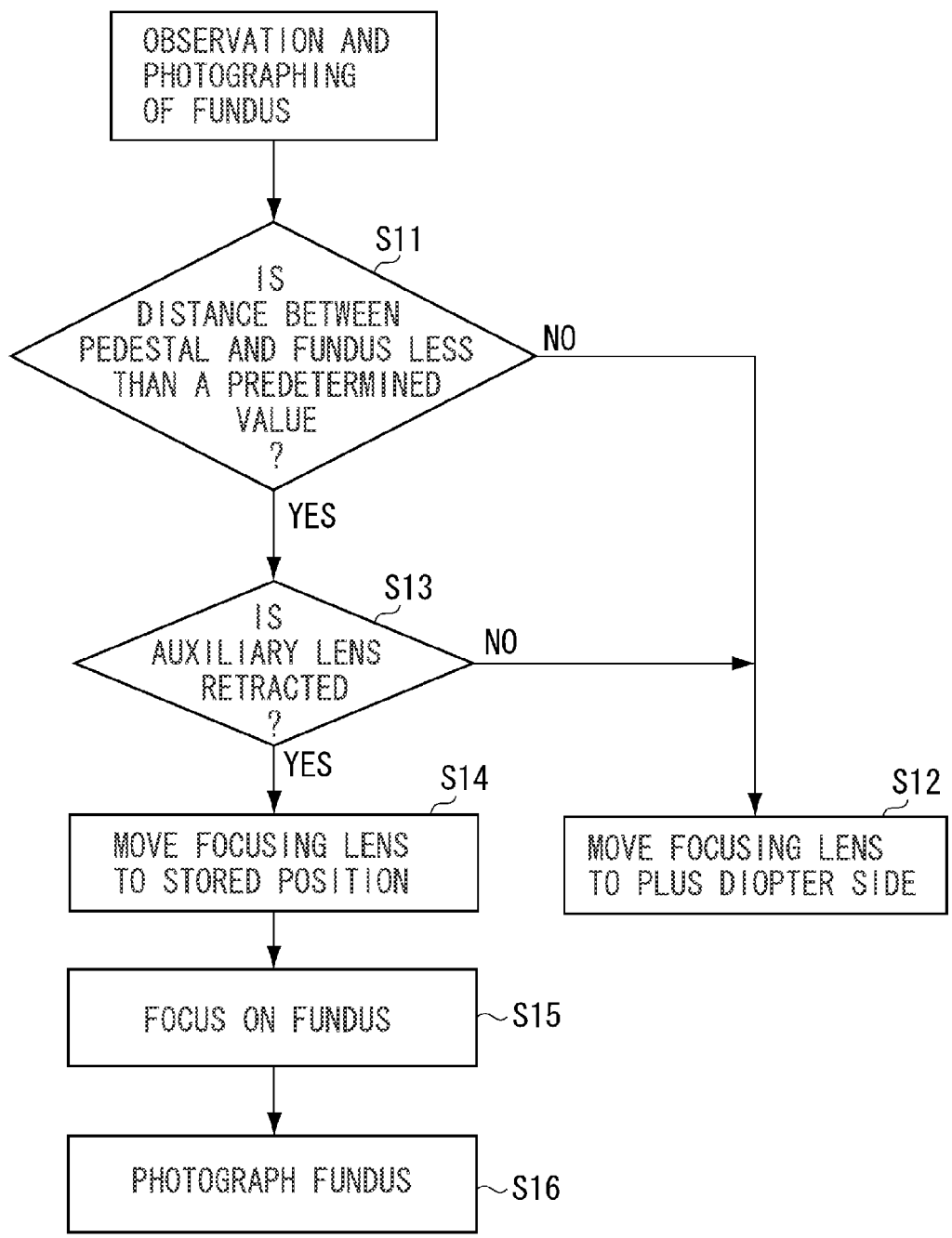
FIG. 6 is a flowchart illustrating an operation of observing and photographing a fundus.

FIG. 6 is a flowchart illustrating the operation of observing a fundus and photographing the fundus. When the fundus is observed and photographed, the operator operates to allow the main body 33 to be close to the subject S by the operation stick 34 and the pedestal position detection unit 25 after the operator retracts the auxiliary lens 17 from the optical path. In step S11, the control unit 22 confirms the position of the pedestal 32 to the subject S. When the distance between the subject S and the pedestal is a predetermined value or more (NO in step S11), the control unit 22 moves the focusing lens 18 to the plus diopter side in step S12. When it is determined that the distance between the pedestal 32 and the subject is less than the predetermined value (YES in step S11), the control unit 22 determines whether the auxiliary lens 17 is retracted from the optical path in step S13. When it is determined that the auxiliary lens 17 is not retracted from the optical path (NO in step S13), the processing proceeds to step S12.

When it is determined in step S13 that the auxiliary lens 17 is retracted from the optical path (YES in step S13), the processing proceeds to step S14. The control unit 22, which has detected the retraction of the auxiliary lens 17 from the optical path by the auxiliary lens insertion detection unit 21, moves the focusing lens 18 to a predetermined position stored in the focus position storing unit in step S14. Then, in step S15, the operator operates the operation stick 34, while observing the fundus on the monitor 24, to accurately align the position to the subject's eye and perform accurate focusing by the focusing lens 18. In this way, the operator confirms the photographing range.

The above-mentioned operation is performed with infrared light, which is emitted from the halogen lamp 1 and from which the visible light is cut. In step S16, the operator observes the image of the fundus on the monitor 24, and confirms that the photographing range and focusing are satisfactory. Thereafter, the operator operates the photographing switch 26 to photograph a still image after allowing the xenon tube 5 to emit light. In this case, the fundus is irradiated with photographing light having a light quantity suitable for the fundus.

In the present exemplary embodiment, the auxiliary lens 17 is provided in the optical path to be inserted into or retracted from the optical path. However, the diopter correction lens 16 that enlarges the focusing range may also be used as the auxiliary lens 17. The order of the detection of the position of the main body 33 and the detection of the insertion state of the auxiliary lens 17 in the flowcharts in FIGS. 5 and 6 is not limited to the one in the flowcharts in FIGS. 5 and 6. The detection of the insertion state of the auxiliary lens 17 may be executed first.

The quantity of light during the changeover between the observation of the anterior segment and the observation of the fundus may be set by controlling a quantity of emitted light from the light source, or may be set in conjunction with the changeover between the crystallite lens diaphragm 8 illustrated in FIG. 2A and the crystallite lens diaphragm 8' illustrated in FIG. 2B.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-199969 filed Aug. 31, 2009, which is hereby incorporated by reference herein in its entirety.

What is claimed is:

1. An ophthalmologic photographing apparatus comprising:
    an optical system configured to observe and photograph a subject's eye;
    an auxiliary lens configured to be able to be inserted into and retracted from the optical system;
    a focusing lens configured to focus the optical system on the subject's eye;
    a focusing lens driving unit configured to move the focusing lens along an optical axis of the optical system;
    an auxiliary lens insertion detection unit configured to detect that the auxiliary lens is inserted into the optical system and the auxiliary lens is retracted from the optical system;
    a storage unit configured to store a position of the focusing lens; and
    a control unit configured to cause the focusing lens driving unit to move the focusing lens to a predetermined position being a position stored in the storage unit in a case where the auxiliary lens insertion detection unit detects retraction of the auxiliary lens, and to cause the focusing lens driving unit to move the focusing lens toward a side of the subject's eye in a case where the auxiliary lens insertion detection unit detects insertion of the auxiliary lens.

2. The ophthalmologic photographing apparatus according to claim 1, wherein the auxiliary lens is also used as a diopter correction lens configured to enlarge a focusing range of the optical system.

3. The ophthalmologic photographing apparatus according to claim 1, wherein the position of the focusing lens stored in the storage unit is a position of the focusing lens that was stored when observation of a fundus was changed to observation of an anterior segment.

4. The ophthalmologic photographing apparatus according to claim 2, wherein the position of the focusing lens stored in the storage unit is a position of the focusing lens that was stored when observation of a fundus was changed to observation of an anterior segment.

5. An ophthalmologic photographing method comprising:
    driving a focusing lens along an optical axis of an optical system configured to observe and photograph a subject's eye;
    focusing the optical system on the subject's eye using the focusing lens;
    storing a position of the focusing lens in a storage unit;
    detecting that an auxiliary lens is inserted into the optical system and the auxiliary lens is retracted from the optical system; and
    photographing a subject's eye with the optical system,
    wherein the focusing lens is driven to a predetermined position being a position stored in the storage unit in a case where the retraction of the auxiliary lens is detected, and is driven toward a side of the subject's eye in a case where insertion of the auxiliary lens is detected.

6. The ophthalmologic photographing method to claim 5, wherein the auxiliary lens is also used as a diopter correction lens configured to enlarge a focusing range of the optical system.

7. The ophthalmologic photographing method according to claim 5, wherein the position of the focusing lens stored in the storage unit is a position of the focusing lens that was stored when observation of a fundus was changed to observation of an anterior segment.

8. The ophthalmologic photographing method according to claim 6, wherein the position of the focusing lens stored in the storage unit is a position of the focusing lens that was stored when observation of a fundus was changed to observation of an anterior segment.

* * * * *